US00PP09283P

United States Patent [19]

Schmidt

[11] Patent Number: Plant 9,283

[45] Date of Patent: Sep. 12, 1995

[54] *CORNUS KOUSA* (DOGWOOD) TREE: 'SCHMRED'

[76] Inventor: James F. Schmidt, 32010 SE. Kelso Rd., Boring, Oreg. 97009

[21] Appl. No.: 311,555

[22] Filed: Sep. 23, 1994

[51] Int. Cl.[6] ..... A01H 5/00
[52] U.S. Cl. ..... Plt./53.2
[58] Field of Search ..... Plt. 53.2

[56] References Cited

U.S. PATENT DOCUMENTS

P.P. 8,676 4/1994 Schmidt ..... Plt./53.2

OTHER PUBLICATIONS

Jaynes, et al Kousa Dogwood, American Nurseryman, Nov. 15, 1993, pp. 40–47.

*Primary Examiner*—James R. Feyrer
*Attorney, Agent, or Firm*—Eugene D. Farley

[57] ABSTRACT

A new and distinct variety of *Cornus kousa* (dogwood) tree charaterized principally by the deep and persistent red-purple color of its efflorescence.

1 Drawing Sheet

This invention relates to a new and distinct variety of *Cornus kousa* (dogwood) tree named Schmred.

The circumstances relating to the discovery of my new dogwood tree are as follows:

I discovered this tree growing in a cultivated area of my nursery in Boring, Oreg. It grew as a random chance seedling among a group of hundreds of other Cornus kousa seedlings I had planted in rows in my nursery. The seed source was undocumented. The seed was used in normal nursery production and not as part of a selection or breeding program. The tree was discovered as a chance seedling growing in cultivation in a nursery row.

My attention was first drawn to this tree when it began to flower. It stood out immediately from a distance because its flower bracts were a deep shade of red-purple and contrasted with the other seedling *Cornus kousa* specimens which all had white flower bracts. *Cornus kousa* flower bracts are normally white. Occasionally a few seedling trees will produce flower bracts which are of a light shade of pink. However, I had grown *Cornus kousa* for years and I had never seen one before with red-purple flower bracts.

I immediately recognized the importance of this new flower color and initiated propagation by budding onto seedling *Cornus kousa* rootstock. When these new vegetatively propagated plants of my *Cornus kousa* variety flowered, they, too, produced deep red-purple flower bracts. Subsequent vegetative propagation in my nursery by both budding and grafting onto seedling understock over a period of six generations has proven the features of my new dogwood variety to be firmly fixed.

In the prior art, there have been described a few *Cornus kousa* selections with pink flower bract color, noteably 'Satomi', 'Dwarf Pink', and 'Rosea'. However, none of these possesses the same combination of characteristics as my new cultivar. Noteably, these previous selections have flower bracts of much a lighter shade than mine, and the color tends to fade considerably in full sunlight, while mine maintains a rich red-purple coloration in full sun. Also, these cultivars do not have the unusually broad and rounded flower bract shape which is characteristic of my new cultivar.

Other distinctive features of my new Cornus kousa variety are as follows:

Oval to broadly oval flower bracts vs. ovate.

Flower bract tip obtuse to rounded vs. acute to acuminate.

Earlier and heavier blooming than typical of the species.

Fruit that colors and ripens two weeks ahead of normal for the species.

A longer flowering season, from early May to mid July in my nursery. Ordinary seedlings usually are finished blooming by late June.

A leaf base that is broadly acute to rounded vs. cuneate to acute.

Leaves that are shorter and broader than the species.

A botanical description in greater detail of my new Cornus kousa (dogwood) tree variety follows.

The description is made with particular reference to the single FIGURE of the drawings, comprising a photograph of my ne *Cornus kousa* (dogwood) tree in full flower. All colors are cited from the R.H.S. Colour Chart.

BOTANICAL DESCRIPTION

Tree shape: An upright, spreading, small tree with branches that tend to grow in a layered appearance in the horizontal plane. The ultimate size of the tree is not known. However, because of its growth rate, the ultimate size is expected to be similar to that of the species, tpically forming a 6–10 meter tall tree under cultivated conditions. Its spread is expected to equal its height.

Tree habit description: The tree typically is single trunk with low branching. The branching is opposite. The central leader is weakly dominant, ascending to about 2 meters before losing its dominance. The tree is heavily branched with branches originating from 45 degree crotch angles then spreading upward and outward. Near the tip of the branches, the growth becomes divided into numerous fine, small branches which tend to be clustered, giving the tree its horizontally layered appearance. The overall crown form is widely rounded.

Branching characteristics: The average number of primary branches originating along 1 meter of trunk of the middle of a 2 meter tall tree is 17. The average number of secondary branches originating along a 50 cm. length of a primary branch of a 2 meter tree is 14. The internodel length averages 10 cm. The crotch angle of the branches varies from 35–50 degrees, with 45 degrees being the average.

Trunk: Sturdy, tending to be low branched.

Bark: Rough textured, with mature bark exfoliating in patches to reveal light colored, smoother, immature bark below. The exfoliation of bark produces an attractive mosaic pattern. Although the exfoliation of the bark is pleasing ornamentally, it is not significantly different from that of the species.

*Mature bark color.*—Greyed-green 197A to Grey-brown 199B.

*Immature bark patches.*—Greyed-orange 164B to 164C.

Current season branches: Long, slender, branching freely at the nodes. Mature growth is greyed-orange, 174A. Immature twigs are Greyed-purple 183A on the side exposed to the sun and Yellow-green 144A on the underside. Glabrous.

Leaves: Opposite, simple broadly ovate, 5–10 cm long by 4–7 cm wide. Leaf base is broadly acute to rounded. The angle formed by the leaf base is 70 to 130 degrees. Leaf tip is acuminate. Leaf margin is finely undulate. Leaf is sparsely and minutely pubsecent above and below. Leaf surface is undulate. Sumemr leaf color is Green 137A on the upper surface and Green 137C to Yellow-green 146B on the underside. Newly unfolding leaves in the spring are tinted Greyed-purple 183A to 183B. Fall color is Red 46A to Red-purple 59A. Measurement of 20 randomly selected leaves of my cultivar and those of typical seedling *Cornus kousa* revealed the following difference in average leaf size and shape:

*'Schmred'.*—7.5 cm long by 5.7 cm wide, length:-width ratio 1.32 to 1.

*Species.*—9.6 cm long by 4.9 cm wide, length:width ratio 1.96 to 1.

Petioles: Short, stout, 5–10 mm long by 2 mm thick. Yellow green 144C, with a Greyed-purple 185C tint where exposed to full sun.

Buds: Vegetative buds are valvate, narrow, with an acutely pointed tip. Flower buds are fatter, ovoid, covered by two valvate scales.

Blooming characteristics: 'Schmred' blooms earlier and longer than the species. In Boring, Oreg. it normally blooms from May 10 to August 1st. The species typically blooms from May 20 to July 1st in the same location. In addition, Schmred will occasionally bloom a second time in September although this second blossoming is dependent on favorable weather and is not to be expected every year. The density of flowers is the same as the species in numbers of flowers. However, Schmred appears more floriferous, because the flowers are larger. Nursery grown trees grown in Boring, Oreg. normally produce blooms in their third year. Typically, seedling *Cornus kousa* do not bloom until the fourth season under the same conditions.

Flowers: The true flowers are tiny and inconspicuous, produced in a 15–20 mm rounded umbel. This umbel is surrounded by four large, showy petaloid bracts, which are commonly referred to as the "flower." The bracts average 5 cm long by 3 cm wide, producing an inflorescence with an average diameter of 11 to 12 cm. The bracts are oval to broadly oval with an acute base and an obtuse to rounded tip. The apex of the bracts forms an obtuse angle, typically of 90 to 110 degrees. The apex of the bracts of the seedlings forms an acute angle, typically of 30 to 60 degrees. The color of the apices of the bracts is Red-purple 60A to 60B. The color of the apex is the same as the full bract when the bracts are fresh. As the bract fades with age, the apex maintains its original color with little or no fading while the full bract fades. It thus appears darker than the full bract at this stage.

Fruit: A red, rounded drupe, 2 cm diameter, borne on a 7 cm stalk. The fruit color is Red-purple 60B to 61B. The fruit normally colors by August 15 and ripens fully by September 25. The fruit of the species normally colors by August 30 and ripens fully by October 15.

Seed: Typical of the species.

Growth rate: Moderate, equal to that typical of the species.

Parentage; Unknown. Chance seedling.

I claim:

1. A new and distinct cultivar of *Cornus kousa* (dogwood) tree, as illustrated and described.

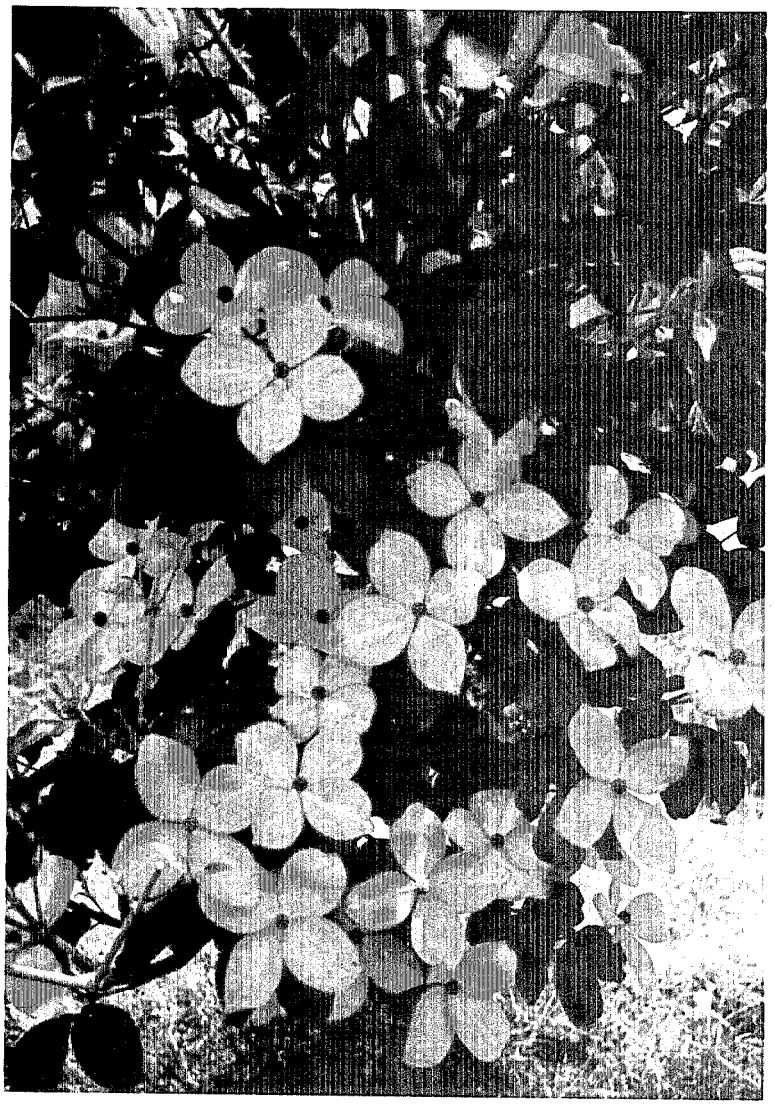

* * * * *